United States Patent [19]

Baker

[11] 4,191,616

[45] Mar. 4, 1980

[54] PURIFICATION PROCESS

[75] Inventor: Brian Baker, Middlesbrough, England

[73] Assignee: Imperial Chemical Industries Limited, London, England

[21] Appl. No.: 969,435

[22] Filed: Dec. 14, 1978

[30] Foreign Application Priority Data

Dec. 19, 1977 [GB] United Kingdom ............... 52727/77

[51] Int. Cl.$^2$ ......................... B01D 3/36; C07C 51/46
[52] U.S. Cl. ........................................ 203/44; 203/48; 203/69; 203/91; 562/593
[58] Field of Search .................... 203/69, 47, 48, 95, 203/44, 91; 562/593

[56] References Cited

U.S. PATENT DOCUMENTS

| | | | |
|---|---|---|---|
| 2,398,485 | 4/1946 | Wilson | 562/593 |
| 3,036,126 | 5/1962 | Chafetz | 203/69 |
| 3,036,127 | 5/1962 | Chafetz | 203/47 |
| 3,180,878 | 4/1965 | Campbell et al. | 562/593 |
| 3,511,757 | 5/1970 | Costain et al. | 562/593 |
| 3,551,300 | 12/1970 | Longley | 562/593 |

*Primary Examiner*—Wilbur L. Bascomb, Jr.
*Attorney, Agent, or Firm*—Cushman, Darby & Cushman

[57] ABSTRACT

Alkane dicarboxylic acids of at least 4 carbon atoms particularly the mixture of succinic, glutaric and adipic acids obtained as byproduct in the manufacture of adipic acid are purified by co-distillation with an alkylbenzene having an atmospheric pressure boiling point of 300° to 350° C. especially dodecylbenzene.

10 Claims, No Drawings

PURIFICATION PROCESS

This invention relates to the purification of dicarboxylic acids, especially mixtures of such acids and more especially mixtures of such acids obtained as by-products in the manufacture of adipic acid by oxidation of suitable feedstocks.

According to our invention a process for the purification of an alkane dicarboxylic acid having at least 4 carbon atoms comprises co-distillation of the said acid with an alkylbenzene having an atmospheric pressure boiling point within the range 300° to 350° C.

The said alkylbenzenes may be mono- or di-alkylbenzenes. Particularly suitable is dodecylbenzene of atmospheric pressure boiling point 330° C. Other suitable alkylbenzenes are undecylbenzene, tridecylbenzene and dodecyltoluene.

Alkane dicarboxylic acids which may be purified according to the process of our invention include succinic acid, glutaric acid, adipic acid, pimelic acid, suberic acid, methylglutaric acid and ethylsuccinic acid. The process may also be used for the purification of mixtures of two or more of such acids to obtain purified mixed acids or, with suitable fractionating during the distillation, purified separated acids.

The process is of particular value, however, for the purification of by-product mixtures of alkane dicarboxylic acids obtained in the manufacture of adipic acid by the oxidation of a suitable feedstock. Adipic acid may be obtained by the oxidation of cyclohexane with oxygen or a gas mixture containing oxygen in a lower aliphatic carboxylic acid solvent, for example acetic acid, in the presence of a catalyst, for example a cobalt catalyst. More especially it may be obtained by the oxidation of cyclohexanol or cyclohexanone, or mixtures thereof, with nitric acid in the presence of a metallic catalyst, especially a mixed copper-vanadium catalyst. Mixed alkane dicarboxylic acids may result as by-products in such oxidations. In particular, in the manufacture of adipic acid by the nitric acid oxidation of cyclohexanol and/or cyclohexanone, adipic acid crystallises from the reaction mixture on cooling leaving a mother liquor which is recycled for re-use in the manufacture after bringing the nitric acid up to its original strength. Since, however, continual recycle of the mother liquor leads to the build-up of impurities in the reaction mixture to an unacceptable level, it is necessary to take a purge of the mother liquor from time to time in order to control the impurity level. Apart from nitric acid, catalyst and residual adipic acid, the principal constituents of the purge are succinic acid and glutaric acid. There have been various proposals for treating the purge in order to isolate useful components from it in a relatively pure state whether for recycle to the oxidation process or not. Nitric acid is commonly removed by evaporation, advantageously under reduced pressure as a first step. In order to assist in the removal of the nitric acid and the decomposition of metal nitrates (from the catalyst metals) it is often preferred to add a non-volatile mineral acid such as sulphuric acid or phosphoric acid prior to the evaporation step so converting the catalyst metals on heating to their sulphates or other non-nitrate salts.

After the removal of nitric acid by evaporation, adipic acid may be allowed to crystallise in the residue and be separated. The adipic acid so obtained may be recycled to the oxidation or otherwise made use of with or without further preliminary refining treatment. The residue remaining after separating this adipic acid still includes adipic acid as well as succinic acid, glutaric acid and catalyst metals.

The purge waste acid may be disposed of to waste, for example by dumping or burning, but this may be environmentally objectionable. Various methods have been proposed for isolating useful organic constituents of acceptable purity from the waste, the principal difficulties arising from the dark colour of the waste and the presence of toxic catalyst metals. Although, in principle, distillation is a suitable purification method, the high boiling points of the dicarboxylic acids, especially of adipic acid, make the complete achievement of purification by distillation alone difficult particularly as the acids tend to change into their anhydrides at the high temperature of the distillation. Accordingly distillation has been limited to the succinic and possibly also the glutaric constituents leaving the adipic constituent to be purified in other ways. Alternatively the dicarboxylic acids have first been converted to their esters, especially the dimethyl esters which, because of their lower boiling points, can be purified, and if desired separated, by distillation. Such multi-stage methods of purification are, however, expensive to operate. It has also been proposed in BP 1,004,131 and U.S. Pat. Nos. 3,036,126 and 3,036,127 to use certain organic liquids capable of forming azeotropes with succinic anhydride in order to assist in the separation of this dibasic acid, but azeotropic distillation has not previously been suggested for the whole of the mixture.

According to our invention, however, purge waste acid from adipic acid manufacture may be co-distilled with an alkylbenzene of atmospheric pressure boiling point 300° to 350° C. to obtain a purified mixture of adipic, glutaric and succinic acids, or by the use of a suitable fractionating column during the distillation the purified, separated acids may be obtained. In either case the products are free from metal catalyst contamination and are essentially free of colour contaminations.

The process of our invention is effected by adding the said alkylbenzene to the dicarboxylic acid or mixture of dicarboxylic acids and distilling the resulting mixtures. Distillation is preferably effected under reduced pressure, for example at pressures of from 10 to 250 mbar. Distillation may be effected through a fractionating column especially where it is desired to separate individual carboxylic acids from mixtures. The contents of the still boiler are preferably agitated. The proportion of said alkylbenzene to dicarboxylic acid in the still is not important provided the said alkylbenzene is always present. The process is particularly suitable for continuous operation, and when so operated the said alkylbenzene is separated from the product and recycled to the still. However, continuous separation and recycle of the said alkylbenzene may be practised even with batch distillation. In these cases the sole net consumption of the said alkylbenzene is that due to adventitious losses. Conveniently the proportion of the said alkylbenzene to dicarboxylic acid in the still is in the range 1:5 to 5:1 preferably about 1:1 by weight.

The distillate is condensed. Preferably the condensate, as a hot liquid, is mixed with water to dissolve the dicarboxylic acid and the said alkylbenzene is separated by conventional liquid-liquid separation means and recycled to the distillation. The water used for dissolving the dicarboxylic acid is conveniently hot, for example from 50° to 100° C. or even higher, for example up to 150° C., if the vessel used as the dissolver is operated under pressure. The dissolver is preferably agitated. The aqueous solution of dicarboxylic acid may be concentrated if desired, for example in a vacuum evaporator, and is then cooled to allow the dicarboxylic acid to crystallise. The crystallised dicarboxylic acid is then separated from the mother liquor by conventional solid-liquid separation means for example by filtration or centrifuging; the solid dicarboxylic acid may be dried if desired and the mother liquor may be recycled to the dissolver. Where a mixture of dicarboxylic acids is treated according to our process and fractionated during the distillation the condensed fractions are, of course, treated separately with water.

when the process of our invention is used for the purification of waste acids from adipic acid manufacture to give a mixture of adipic, glutaric and succinic acids, the waste acids are preferably added to the still in the molten condition, since the mixture is isolated from the adipic acid manufacture in this condition, for example at a temperature within the range 120° to 160° C. The still is conveniently operated at a reduced pressure e.g. of about 133 mbar, and on heating the still boiler contents at this latter pressure to about 230° C. the azeotrope of, for example, dodecylbenzene and dicarboxylic acid distils at a temperature in the approximate range 202° to 212° C. It is advantageous to segregate the forerun of azeotrope, for example the first 10% by weight, which may be discoloured, though the alkylbenzene it contains may be separated, for example by water washing and conventional separation, and returned to the still. The condensed azeotrope is run into water in the dissolver, which is preferably hot e.g. in excess of 50° C. preferably approximately 80° C., the ratio of water to azeotrope being preferably 10:1 to 2:1 typically about 5:1 by weight. The said alkylbenzene is continuously drawn off from the dissolver and returned to the still. The aqueous solution of dicarboxylic acid from the dissolver is then concentrated e.g. to about ¾ of its volume, and cooled, for example to about 10° C. to allow the dicarboxylic acids to crystallise. The solid mixture of dicarboxylic acids is then separated.

The still residues consist of catalyst metals and other impurities and may be discarded or treated to recover the catalyst metals. By this means a colourless mixture of adipic, glutaric and succinic acids is obtained in a recovery of up to approximately 90% based on the weight of the waste acids.

The invention is illustrated but not limited by the following Example.

EXAMPLE

A sample of waste acids from adipic acid manufacture had the following composition:

| | |
|---|---|
| Adipic acid | 25.3% by weight |
| Glutaric acid | 55.6% by weight |
| Succinic acid | 17.1% by weight |
| Mineral acid (H$_2$SO$_4$ + HNO$_3$) | 1.5% by weight |
| Metals (Cu + V) | 500ppm by weight | and consisted of a greenish coloured solid.

1000 g. of the sample and 1200 ml of dodecylbenzene were charged to a boiler which was stirred and the contents distilled at 133 mbar pressure without the use of a column. The first 120 g. of "fores" containing 35 g. of impure dibasic acids were rejected and four fractions were collected as specified in the following Table. The dodecylbenzene collected between the fractions was recycled to the boiler. The fractions were discharged into water the dodecylbenzene was separated, the aqueous portions were concentrated and the dibasic acid was allowed to crystallise and was separated. The composition of the crystallised dibasic acid fractions is given in the following Table. The total weight of crystallised dibasic acids obtained was 702 g. of white material free of metal and mineral acid contamination. Further concentration of the aqueous liquors gave a further 150 g. of slightly off-white acid. There were residues of 45 g. in the still and 36 g. in the catchpot.

TABLE

| Fraction No. | Wt of azeotrope (g) | Wt of acid in azeotrope (g) | Wt % acid in azeotrope | Analysis of recrystallised acid (wt %) | | |
|---|---|---|---|---|---|---|
| | | | | A | G | S |
| 1 | 888 | 293 | 33.0 | 0 | 12.6 | 87.4 |
| 2 | 851 | 245 | 26.1 | 7.5 | 88.9 | 3.5 |
| 3 | 979 | 208 | 21.2 | 35.9 | 63.9 | 0 |
| 4 | 1002 | 138 | 13.8 | 97.6 | 2.3 | 0 |

A = Adipic Acid,
G = Glutaric Acid,
S = Succinic Acid

I claim:

1. A process for the purification of an alkane dicarboxylic acid having at least 4 carbon atoms which comprises co-distilling said acid with an alkylbenzene having an atmospheric pressure boiling point within the range 300° to 350° C.

2. A process according to claim 1 in which the alkylbenzene is a mono- or di-alkylbenzene.

3. A process according to claim 2 in which the alkylbenzene is dodecylbenzene, undecylbenzene, tridecylbenzene or dodecyltoluene.

4. A process according to claim 1 in which the alkane dicarboxylic acid is succinic acid, glutaric acid, adipic acid, pimelic acid, suberic acid, methylglutaric acid, ethylsuccinic acid or a mixture of two or more of such acids.

5. A process according to claim 1 in which the co-distillation is carried out under reduced pressure.

6. A process according to claim 1 in which the proportion of alkylbenzene to dicarboxylic acid in the co-distillation is about 1:1 by weight.

7. A process according to claim 1 in which the distillate from the co-distillation is mixed with water to dissolve the dicarboxylic acid.

8. A process according to claim 1 for the purification of a mixture of acids containing adipic, glutaric and succinic acids which is obtained as a byproduct of the manufacture of adipic acid in which the mixture of acids is added to the co-distillation in a molten condition at a temperature in the range 120° to 160° C., the co-distillation being carried out at a pressure of about 133 mbar in a still in which the still contents are held at about 230° C.

9. A process according to claim 8 in which the condensed azeotrope from the co-distillation is run into water the temperature of which is 50° to 150° C. and the ratio of water to azeotrope is about 5:1 by weight.

10. A process according to claim 9 in which the alkylbenzene is separated from the water and returned to the co-distillation and the aqueous solution of dicarboxylic acids is concentrated and cooled to allow the dicarboxylic acids to crystallise.

* * * * *